US00PP34390P2

(12) United States Plant Patent
Koot

(10) Patent No.: US PP34,390 P2
(45) Date of Patent: Jun. 28, 2022

(54) ***PETUNIA* PLANT NAMED 'DOPETDURASOPI'**

(50) Latin Name: ***Petunia* X *hybrida***
Varietal Denomination: Dopetdurasopi

(71) Applicant: DUMMEN GROUP B.V., De Lier (NL)

(72) Inventor: Arjan Koot, Oeffelt (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 17/246,518

(22) Filed: Apr. 30, 2021

(51) Int. Cl.
*A01H 5/02* (2018.01)
*A01H 6/82* (2018.01)

(52) U.S. Cl.
USPC ..... Plt./356.21

(58) Field of Classification Search
USPC ..... Plt./356.21
CPC ... A01H 5/02; A01H 5/00; A01H 6/82; A01H 6/824; A01H 6/1424; A01H 6/42
See application file for complete search history.

(56) References Cited

PUBLICATIONS

Carlin Horticultural Supplies 2021 Galema Liner Program, retrieved on Jul. 19, 2021, retrieved from the Internet at https://www.carlinsales.com/pdf/plug%20days/GalemaProgram2021.pdf, pp. 1-4,24,35-37. (Year: 2020).*

Dummen Orange for you Annuals 2021-2022, retrieved on Jul. 19, 2021, retrieved from the Internet at https://na.dummenorange.com/app/pdfcatalogs/detail.web?catalogId=135, cover page, pp. 236-239. (Year: 2021).*

* cited by examiner

*Primary Examiner* — June Hwu
(74) *Attorney, Agent, or Firm* — C. Anne Whealy

(57) ABSTRACT

A new and distinct cultivar of *Petunia* plant named 'Dopetdurasopi', characterized by its relatively compact, upright and mounding to hanging plant habit; moderately vigorous growth habit; freely branching habit; early and freely flowering habit; large light purplish pink-colored flowers with darker purplish red-colored centers and venation; and good garden performance.

1 Drawing Sheet

Botanical designation: *Petunia* X *hybrida*.
Cultivar denomination: 'DOPETDURASOPI'.

STATEMENT REGARDING PRIOR DISCLOSURES BY INVENTOR/APPLICANT & ASSIGNEE

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Petunia* plant, botanically known as *Petunia* X *hybrida* and hereinafter referred to by the name 'Dopetdurasopi'.

The new *Petunia* plant is a product of a planned breeding program conducted by the Inventor in Rheinberg, Germany. The objective of the breeding program is to create new compact, freely branching and early-flowering *Petunia* plants with numerous attractive flowers.

The new *Petunia* plant originated from a cross-pollination made by the Inventor in July, 2019 in Rheinberg, Germany of a proprietary selection of *Petunia* X *hybrida* identified as code number TT13-002214-006, not patented, as the female, or seed, parent with a proprietary selection of *Petunia* X *hybrida* identified as code number TT17-140131-001, not patented, as the male, or pollen, parent. The new *Petunia* plant was discovered and selected by the Inventor as a single flowering plant from within the progeny of the stated cross-pollination in a controlled greenhouse environment in Rheinberg, Germany in May, 2020.

Asexual reproduction of the new *Petunia* plant by terminal vegetative cuttings in a controlled greenhouse environment in Rheinberg, Germany since June, 2020 has shown that the unique features of this new *Petunia* plant are stable and reproduced true to type in successive generations.

SUMMARY OF THE INVENTION

Plants of the new *Petunia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Dopetdurasopi'. These characteristics in combination distinguish 'Dopetdurasopi' as a new and distinct *Petunia* plant:

1. Relatively compact, upright and mounding to hanging plant habit.
2. Moderately vigorous growth habit.

3. Freely branching habit.
4. Early and freely flowering habit.
5. Large light purplish pink-colored flowers with darker purplish red-colored centers and venation.
6. Good garden performance.

Plants of the new *Petunia* can be compared to plants of the female and male parent selections. In side-by-side comparisons, plants of the new *Petunia* differ primarily from plants of the parent selections in flower color as flowers of plants of the new *Petunia* are light purplish pink in color with darker purplish red-colored centers and venation whereas flowers of plants of the parent selections are solid darker pink in color.

Plants of the new *Petunia* can be compared to plants of *Petunia* X *hybrida* 'Sunrove', disclosed in U.S. Plant Pat. No. 14,125. In side-by-side comparisons, plants of the new *Petunia* and 'Sunrove' differ primarily in the following characteristics:

1. Plants of the new *Petunia* are more compact than and not as vigorous as plants of 'Sunrove'.
2. Flowers of plants of the new *Petunia* are light purplish pink in color with darker purplish red-colored centers and venation whereas flowers of plants of 'Sunrove' are light purple in color with reddish purple-colored venation.

BRIEF DESCRIPTION OF THE PHOTOGRAPH

The accompanying colored photograph illustrates the overall appearance of the new *Petunia* plant showing the colors as true as it is reasonably possible to obtain in colored reproductions of this type. Colors in the photograph may differ slightly from the color values cited in the detailed botanical description which accurately describe the colors of the new *Petunia* plant.

The photograph is a side perspective view of a typical flowering plant of 'Dopetdurasopi' grown in a container.

DETAILED BOTANICAL DESCRIPTION

The aforementioned photograph and following observations, measurements and values describe plants grown during the spring in 22-cm containers in a glass-covered greenhouse in Rheinberg, Germany and under cultural practices typical of commercial *Petunia* production. During the production of the plants, day and night temperatures averaged 18° C. and light levels averaged 4,500 lux. Plants were twelve weeks old when the photograph was taken and 25 weeks old when the description was taken. In the following description, color references are made to The Royal Horticultural Society Colour Chart, Fifth Edition, 2007, except where general terms of ordinary dictionary significance are used.

Botanical classification: *Petunia* X *hybrida* 'Dopetdurasopi'.

Parentage:

*Female, or seed, parent*.—Proprietary selection of *Petunia* X *hybrida* identified as code number TT13-002214-006, not patented.

*Male, or pollen, parent*.—Proprietary selection of *Petunia* X *hybrida* identified as code number TT17-140131-001, not patented.

Propagation:

*Type*.—By terminal vegetative cuttings.

*Time to initiate roots, summer*.—About five days at temperatures about 20° C.

*Time to initiate roots, winter*.—About seven days at temperatures about 20° C.

*Time to produce a rooted young plant, summer*.—About three weeks at temperatures about 20° C.

*Time to produce a rooted young plant, winter*.—About four weeks at temperatures about 20° C.

*Root description*.—Fine, fibrous; close to 155B in color, actual color of the roots is dependent on substrate composition, water quality, fertilizers, substrate temperature and age of roots.

*Rooting habit*.—Freely branching; dense.

Plant description:

*Plant and growth habit*.—Relatively compact, upright and mounding to hanging plant habit; freely branching habit with about six primary lateral branches each with about eight to eleven secondary branches developing after pinching; moderately vigorous growth habit; moderate growth rate.

*Plant height, soil level to top of foliar plane*.—About 25 cm.

*Plant height, soil level to top of floral plane*.—About 28 cm.

*Plant diameter*.—About 64 cm.

Lateral branch description:

*Length*.—About 62 cm.

*Diameter*.—About 5 mm.

*Internode length*.—About 1.9 cm.

*Strength*.—Moderately strong.

*Aspect*.—Initially upright to outwardly spreading.

*Texture and luster*.—Pubescent; semi-glossy.

*Color, developing*.—Close to 143B.

*Color, fully developed*.—Close to 146B; at the internodes, close to 143C.

Leaf description:

*Arrangement*.—Before flowering, alternate; after flowering, opposite; simple.

*Length*.—About 4 cm.

*Width*.—About 2.3 cm.

*Shape*.—Spatulate.

*Apex*.—Obtuse.

*Base*.—Attenuate.

*Margin*.—Entire.

*Texture and luster, upper and lower surfaces*.—Pubescent; leathery; semi-glossy.

*Venation pattern*.—Pinnate; arcuate.

*Color*.—Developing and fully expanded leaves, upper surface: Close to 146A; venation, close to 146A. Developing and fully expanded leaves, lower surface: Close to 146B; venation, close to 146B.

*Petioles*.—Length: About 2.5 mm. Diameter: About 2.1 mm. Strength: Moderately strong; firm. Texture and luster, upper and lower surfaces: Smooth, glabrous; matte. Color, upper and lower surfaces: Close to 144C.

Flower description:

*Flower type and flowering habit*.—Single salverform flowers arising from leaf axils; freely flowering habit with usually about 240 flowers and flower buds developing per plant; flowers face mostly upright to outwardly.

*Fragrance*.—None detected.

*Natural flowering season*.—Plants flower continuously during the spring and summer in Germany; early flowering habit, plants typically beginning flowering about nine weeks after planting.

*Flower longevity*.—Individual flowers last about two to three days on the plant; flowers persistent.

*Flower buds*.—Length: About 2.6 cm. Diameter: About 8 mm. Shape: Ovoid. Texture and luster: Rippled; semi-glossy. Color: Proximally, close to 145C and distally, close to 183B.

*Flower diameter*.—About 4.8 cm.

*Flower depth* (*height*).—About 4.6 cm.

*Flower throat diameter*.—About 9.5 mm.

*Flower tube length*.—About 2.25 cm.

*Flower tube diameter, proximally*.—About 2.8 mm.

*Corolla*.—Arrangement: Five petals fused at the base and opening into a flared trumpet. Petal lobe length (from throat): About 2.4 cm. Petal lobe width: About 2.5 cm. Petal shape: Roughly spatulate. Petal apex: Obtuse. Petal margin: Entire; slightly undulate. Petal texture and luster, upper and lower surfaces: Rippled, glabrous; semi-glossy. Throat texture and luster: Rippled, glabrous; semi-glossy. Tube texture and luster: Rippled, pubescent; semi-glossy. Color: Petal lobe, when opening, upper surface: Close to 63D. Petal lobe, when opening, lower surface: Close to 62D. Petal lobe, fully opened, upper surface: Close to 63D; towards the center and venation, close to 57A; main color becoming closer to 62C with subsequent development. Petal lobe, fully opened, lower surface: Close to 62C; venation, close to 62C and 59D; main color becoming closer to 62D with subsequent development. Flower throat: Close to 183D; venation, close to 183B. Flower tube: Close to 195B and 182C; venation, close to 184B.

*Sepals*.—Arrangement: Five sepals fused at the base forming a tubular star-shaped calyx. Length: About 1.4 cm. Diameter: About 2.7 mm. Shape: Oblong. Apex: Rounded. Base: Decurrent. Margin: Entire. Texture and luster, upper and lower surfaces: Smooth, glabrous; semi-glossy. Color: When opening and fully opened, upper surface: Close to 146A. When opening and fully opened, lower surface: Close to 146B.

*Peduncles*.—Length: About 1.5 cm. Diameter: About 1.8 mm. Strength: Moderately strong. Texture and luster: Smooth, glabrous; semi-glossy. Color: Close to 143C.

*Reproductive organs*.—Stamens: Quantity per flower: Five. Filament length: About 1.9 cm. Filament color: Close to 155D. Anther length: About 2 mm. Anther shape: Ovate. Anther color: Close to 158C. Pollen amount: Abundant. Pollen color: Close to 158A. Pistils: Quantity per flower: One. Pistil length: About 2 cm. Style length: About 1.8 cm. Style color: Close to 145D. Stigma diameter: About 1.5 mm. Stigma shape: Rounded. Stigma color: Close to 144B. Ovary color: Close to 144B. Fruits: Quantity produced per plant: About 150 during the flowering season. Length: About 5 mm. Diameter: About 4.5 mm. Texture: Smooth, glabrous. Color: Close to 199D. Seeds: Quantity per flower: About 90. Length: About 0.3 mm. Diameter: About 0.3 mm. Texture: Smooth, glabrous. Color: Close to 200B.

Garden performance: Plants of the new *Petunia* have been observed to have good garden performance and tolerate wind, rain, temperatures ranging from about 5° C. to about 40° C. and to be suitable for USDA Hardiness Zone 11.

Pathogen & pest resistance: To date, plants of the new *Petunia* have not been observed to be resistant to pathogens and pests common to *Petunia* plants.

It is claimed:

1. A new and distinct *Petunia* plant named 'Dopetdurasopi' as illustrated and described.

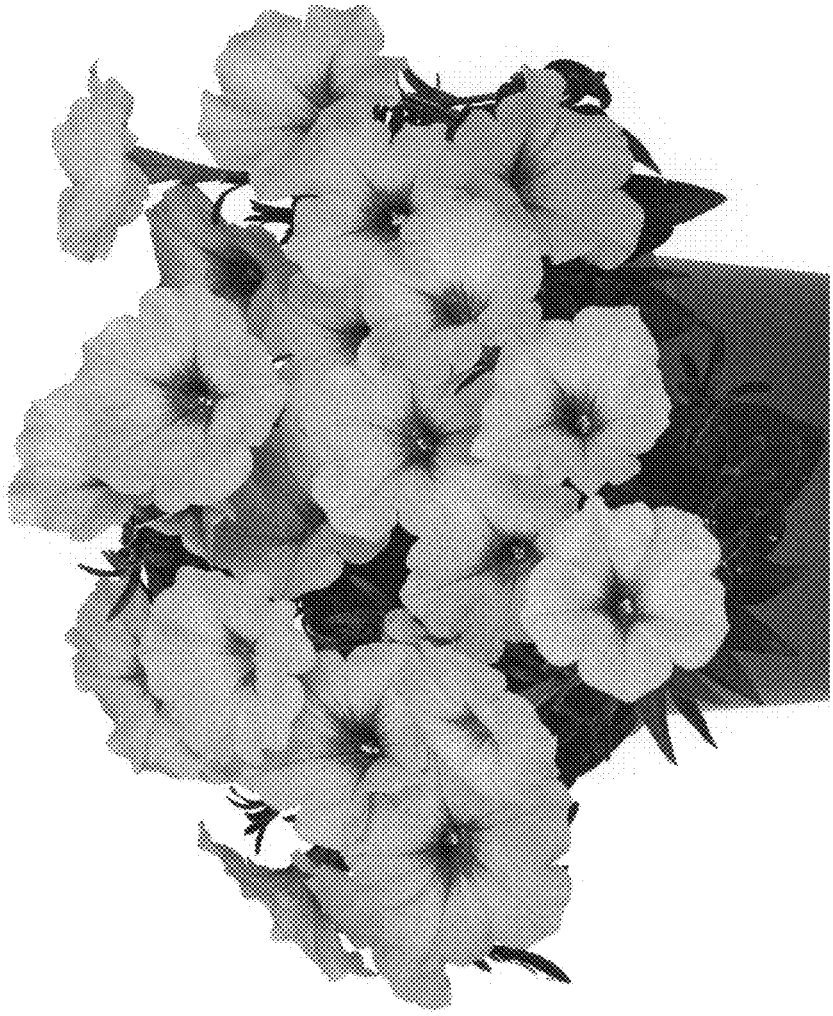

* * * * *